US005316952A

United States Patent [19]

Brimhall

[11] Patent Number: 5,316,952

[45] Date of Patent: May 31, 1994

[54] BLOOD SAMPLE APPARATUS AND METHOD

[75] Inventor: Owen D. Brimhall, South Jordan, Utah

[73] Assignee: Technical Research Associates, Inc., Salt Lake City, Utah

[21] Appl. No.: 656,562

[22] Filed: Feb. 15, 1991

[51] Int. Cl.[5] .............................................. G01N 33/86

[52] U.S. Cl. ........................................ 436/70; 422/72; 422/73; 422/100; 422/102; 436/45; 436/165; 436/177

[58] Field of Search ........................ 422/58, 72, 73, 99, 422/100, 102, 61, 68.1; 436/45, 63, 66, 165, 177, 301, 70; 435/291, 293

[56] References Cited

U.S. PATENT DOCUMENTS 3,168,473 2/1965 Goda et al. ........................... 422/72
3,640,267 2/1972 Hurtig et al. ......................... 422/58
5,039,617 8/1991 McDonald et al. .................. 422/58
5,110,743 5/1992 Windisch et al. ..................... 436/45

*Primary Examiner*—Lyle A. Alexander
*Attorney, Agent, or Firm*—J. Winslow Young

[57] ABSTRACT

An improved blood sample apparatus having a capillary channel formed in a basal element and enclosed with a transparent overlay to create a capillary tube. A chamber for receiving a sample of blood is formed in the basal element at one end of the capillary channel. A blotter is placed in the chamber to receive the sample of blood. An overflow reservoir is formed perpendicularly to the capillary tube and receives surplus blood in excess of that needed to fill the capillary tube. A scale adjacent the capillary tube provides an automatic reading of the hematocrit. The transparent overlay sealingly encloses the sample of blood inside the hematocrit apparatus. The transparent overlay also includes a writing surface and a machine-readable indicia.

14 Claims, 2 Drawing Sheets

BLOOD SAMPLE APPARATUS AND METHOD

FIELD OF THE INVENTION

This invention relates to blood sample apparatus and, more particularly, to a blood sample apparatus for receiving and processing a sample of blood, the apparatus including a blood-receiving chamber, an overflow reservoir, and a capillary tube all of which are in fluid communication.

THE PRIOR ART

Numerous diagnostic techniques are based upon the analysis of a sample of blood. More commonly, one of these routinely used analytical procedures is the determination of the hematocrit of the sample of blood. The term "hematocrit" is used in the field of medicine to refer to the ratio of packed red blood cells in a blood sample. Sedimentation of the red blood cells to separate them from the plasma is accomplished by high-speed centrifugation of the blood sample. During centrifugation the incrementally greater density of the red blood cells results in their becoming packed in the bottom of the centrifugation cavity leaving the plasma as a layer of clear medium above the packed red blood cells. The hematocrit is then determined from the resulting ratio of the volume of the packed red blood cells to the total volume of the sample of blood. To obtain a suitable degree of accuracy, the sample of blood is drawn by capillary action into a capillary tube having a relatively small diameter or capillary. The total length versus total volume of the sample of blood provides improved accuracy for the hematocrit reading.

Other diagnostic procedures are based upon similar processing strategies for the sample of blood. For example, one test for the presence of malaria involves centrifugation of the sample of blood in a capillary tube. Red blood cells infected with the malaria microorganism have an incrementally lower specific gravity than healthy red blood cells with the result that these infected cells will tend to concentrate in the vicinity of the interface between the packed red blood cells and the supernatant plasma. Fluorescence techniques are then employed to ascertain the likelihood of the presence of malaria.

The conventional capillary tube, as the name implies, relies upon the inherent nature of capillary action to draw the sample of blood upwardly into the capillary tube. Glass exhibits excellent surface tension properties necessary for capillary action so that glass is the preferred material of construction for capillary tubes. However, glass is notorious for its fragility so that a capillary tube fabricated from glass can be especially dangerous particularly when blood has been drawn up into the capillary. The risk of breakage is increased by the fact that the end of the capillary tube is pressed into a clay-like material to plug the capillary tube to prevent the leakage of blood. Normal handling of a glass capillary tube has an element of risk, but this risk is compounded when the end of the glass capillary tube is pressed into the clay-like material.

The disastrous increase in the number of cases involving persons infected with the virus responsible for the Acquired Immune Deficiency Syndrome (AIDS) has resulted in the adaption of rigorous measures for handling of blood or blood products. Protective gloves are routinely worn as one of the measures mandated for persons involved in handling blood even in amounts as small as the drop of blood that is drawn into the capillary tube. However, if a glass capillary tube shatters, the broken ends thereof can easily penetrate a conventional latex or plastic glove. Further, protective gloves reduce tactile sensations and manual dexterity and thereby interfere with the safe handling of a capillary tube due to the small size of the capillary tube. Accordingly, there is a corresponding increase in the number of accidental breakages of capillary tubes so that it ultimately becomes problematical whether the wearing of protective gloves provides increased safety or constitutes an occupational hazard.

Correlation between the particular patient and the specific blood sample contained in a capillary tube is always a problem since the conventional capillary tube has essentially no surface upon which the appropriate information can be transcribed. Clearly, the attribution of the wrong information obtained from the particular blood sample to the wrong patient could have catastrophic results. Customarily, this problem is solved by placing the capillary tube in a separate holder with the appropriate information being transcribed on the holder in lieu of on the capillary tube. Great care must be taken to assure that the correct capillary tube is returned to the correct holder at all times. This is particularly important after the capillary tube has undergone centrifugation since a plurality of capillary tubes are subjected to centrifugation simultaneously. Each capillary tube is removed from its respective holder when placed in the centrifuge apparatus.

The centrifugation process alone creates an additional hazard due to its high speed of rotation along with the resulting high gravitational forces imposed on the capillary tube. The high speed of rotation will tend to atomize any exposed blood while the high gravitational forces have been known to cause an imperfectly sealed capillary tube to allow blood to leak past the clay plug. Improperly mounted or loosely held capillary tubes have also been known to shatter during centrifugation. Any one of these events contributes to the creation of an aerosol of atomized blood products. Further, residual amounts of blood are inherently carried on the exterior surface of the capillary tube so that some of this exposed blood can become part of this aerosol of blood products.

In view of the foregoing, it would be a significant advancement in the art to provide a capillary tube apparatus that is essentially unbreakable. It would also be an advancement in the art to provide a capillary tube apparatus for handling a sample of blood wherein the sample of blood is completely sealed inside the capillary tube apparatus thereby eliminating all danger of leakage of the blood not only during centrifugation but also during handling of the capillary tube. Another advancement in the art would be to provide a capillary tube apparatus that is easier to handle and includes an extended surface upon which information can be displayed. An even further advancement in the art would be to provide a capillary tube apparatus whereby the capillary tube includes an overflow reservoir so as to provide an essentially fixed total volume of blood in the capillary tube so that the scale for determining the hematocrit can be placed adjacent the capillary tube. Such a novel apparatus and method is disclosed and claimed here.

BRIEF SUMMARY AND OBJECTS OF THE INVENTION

This invention relates to a novel capillary tube apparatus and method whereby the capillary tube is formed as an elongated channel in a planar element and is enclosed by a transparent overlay. A blood-receiving chamber is formed at one end of the capillary tube and includes a porous medium suitable for holding a blood sample until the capillary tube apparatus is subjected to centrifugation. The chamber is sealable with the transparent overlay so as to completely isolate the blood sample in the capillary tube apparatus. An overflow reservoir receives surplus blood in excess of the blood needed to fill the capillary tube thereby providing the capillary tube with an essentially fixed total volume. An adjacent scale provides for a direct reading of the hematocrit. The planar element also includes a surface upon which information can be displayed.

It is, therefore, a primary object of this invention to provide improvements in apparatus for handling a sample of blood.

It is another object of this invention to provide improvements in the method of handling a sample of blood.

Another object of this invention is to provide an overflow reservoir for the capillary tube thereby providing an essentially fixed total volume for the capillary tube.

Another object of this invention is to provide a scale adjacent the capillary tube so that the hematocrit of the sample of blood in the capillary tube can be read directly from the capillary tube apparatus.

Another object of this invention is to provide a planar element having a capillary groove therein, the planar element providing a handling surface as well as a surface upon which information can be displayed.

Another object of this invention is to provide an apparatus for handling a sample of blood wherein the blood is completely enclosed inside the apparatus.

Another object of this invention is to provide an apparatus for handling a sample of blood wherein the apparatus is designed so as to enable it to be fabricated from an unbreakable plastic material.

These and other objects and features of the present invention will become more readily apparent from the following description in conjunction with the accompanying drawing and the appended claims.

DETAILED DESCRIPTION OF THE PREFERRED EMBODIMENT

The invention is best understood by the following description with reference to the accompanying drawing wherein like parts are designated by like numerals throughout.

General Discussion

The quick, accurate determination of certain parameters of a sample of blood such as its hematocrit is essential for a number of medical procedures. Conventionally, a drop of blood is drawn into a capillary tube by capillary action. The end of the capillary tube is then plugged by being pressed into a clay-like material. The capillary tube is then subjected to centrifugation in a high-speed centrifuge apparatus. The force of centrifugation packs the red blood cells toward the bottom end of the capillary tube thus providing a visual representation of the ratio of packed red blood cells to the total volume of blood in the capillary tube. Since the total length occupied by the blood in the capillary tube varies from sample to sample, the determination of the ratio requires the use of either an optical/electronic system for reading the hematocrit or a nomogram against which the centrifuged blood sample is compared.

The novel blood sample apparatus of this invention has been designed so that the sample of blood is completely enclosed inside the blood handling apparatus. The blood handling apparatus is also configured so that the capillary tube receives an essentially fixed column of blood from the sample of blood thereby accommodating placement of a scale adjacent the capillary tube. The term "capillary" is used herein to indicate the very small bore of the capillary tube and not to imply that the blood sample is drawn therein under the force of capillary action. The hematocrit, for example, can be determined directly from the scale without having to resort to other systems and/or devices to determine the hematocrit. Since it is well known that most plastic materials exhibit poor surface tension capabilities so that it is generally not practicable to draw blood into a capillary tube fabricated from plastic, a blood-receiving chamber is placed in fluid communication with the capillary tube. The blood sample is forced into the capillary tube by the initial centrifugal forces during centrifugation. Surplus blood in the sample is held in an overflow reservoir thereby providing the capillary tube with an essentially fixed length.

DETAILED DESCRIPTION

Figure 1:
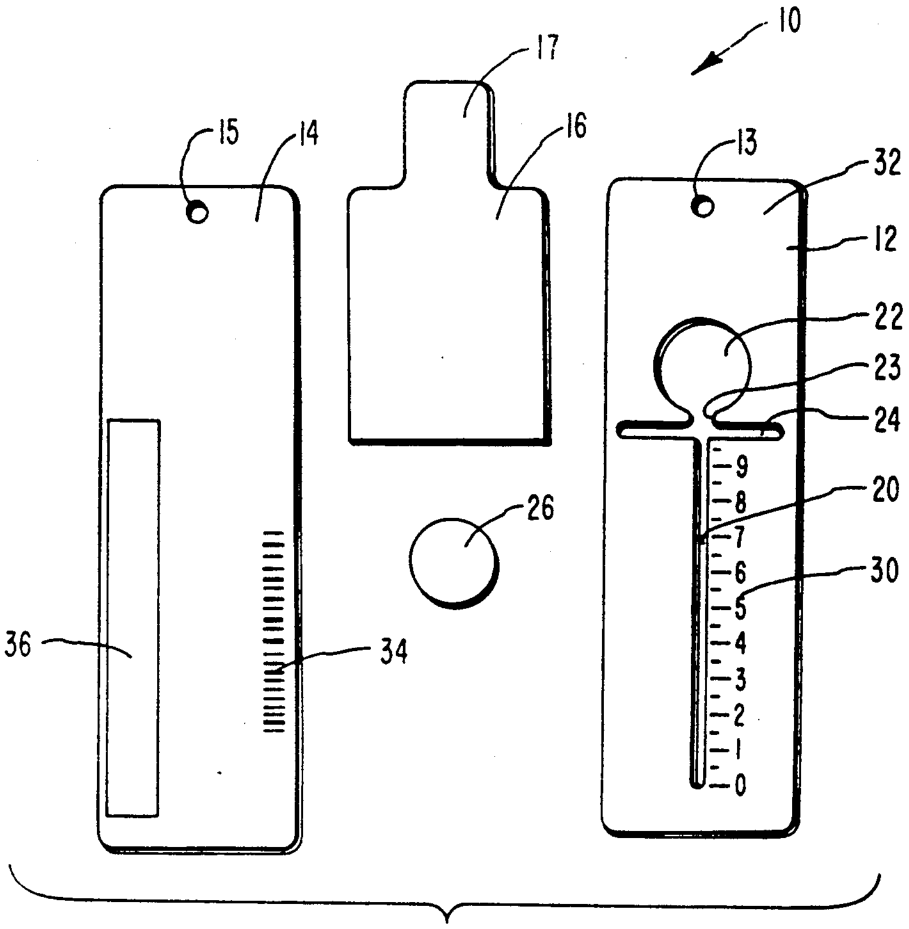
FIG. 1 is an exploded plan view of a presently preferred embodiment of the novel invention of this application showing the relationship between the various components.

Referring now to FIG. 1, the novel blood sample apparatus of this invention is shown generally at 10 and includes a basal element 12, a transparent cover 14, and a removable overlay 16. Basal element 12 is fabricated from a plastic material suitable for use in handling blood (blood sample 50, FIG. 4) and may be fabricated either as a flexible member or with a predetermined degree of rigidity. Basal element 12 is preferentially fabricated with a contrasting color so as to facilitate visual determination of the desired parameters as will be discussed more fully hereinafter. Advantageously, basal element 12 is fabricated from a plastic material that can be readily processed through injection molding, thermoforming, or the like. It is important, however, regardless of the method of manufacture, that the capillary channel that is formed therein, capillary channel 20, is provided with a uniform cross section along its entire length for reasons that will be described more fully hereinafter.

Figure 4:
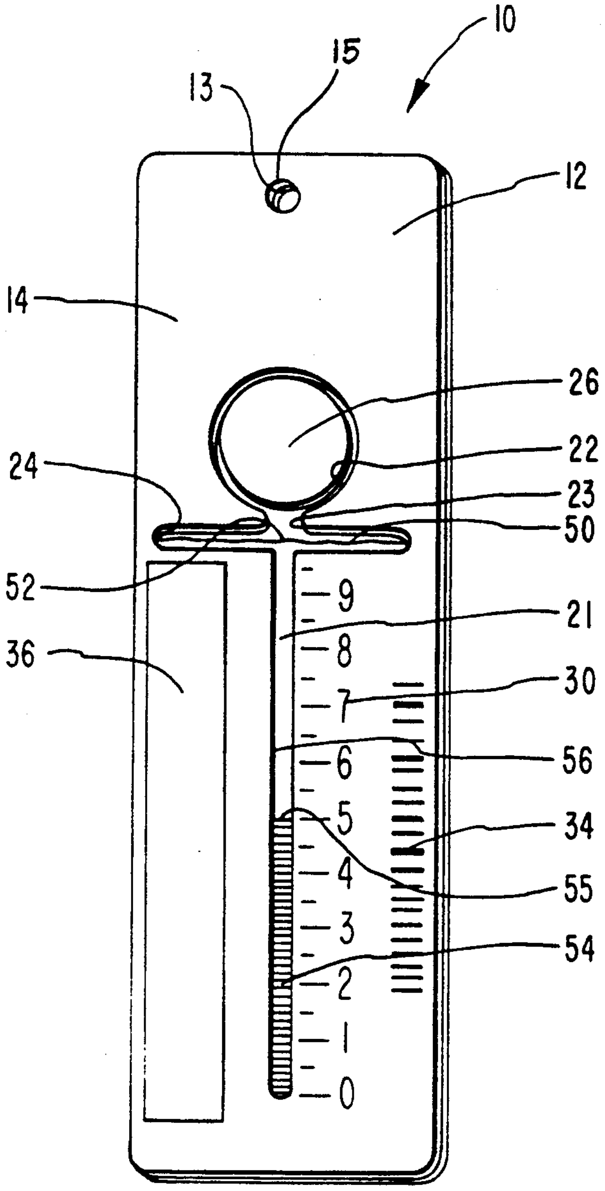
FIG. 4 is a plan view of the hematocrit apparatus after the drop of blood has been subjected to centrifugation.
Figure 5:
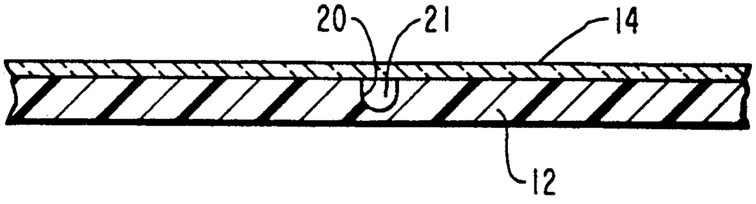
FIG. 5 is an enlarged, cross sectional view taken along lines 5—5 of FIG. 2.

Capillary channel 20 is formed in basal element 12 so as to create an elongated capillary tube 21 when the open face thereof is sealingly closed by transparent cover 14. The resulting capillary tube 21 generally corresponds to a conventional capillary tube (not shown) in as far as the total quantity of blood 50 (FIG. 4) required to fill capillary tube 21. FIG. 5 more clearly shows the interrelationship between capillary channel 20 and transparent cover 14 in the formation of capillary tube 21 out of capillary channel 20.

A blood-receiving chamber 22 is formed in basal element 12 and in fluid communication with capillary channel 20. Chamber 22 is configured as an open well having an actual diameter of about one centimeter. Chamber 22 is configured to receive therein a blotter 26 which is designed to temporarily receive blood 50 (FIG. 4). An overflow reservoir 24 is formed as two arms extending outwardly adjacent the entrance to capillary channel 20. Overflow reservoir 24 is important in that it spreads the overflow blood 50 (FIG. 4) laterally to the axis of capillary channel 20 as will be describe more fully hereinafter. A relatively wide throat 23 extends between chamber 22 and capillary channel 20 for the passage of blood 50 (FIG. 4) from blotter 26 into capillary channel 20. The two arms of overflow reservoir 24 extend outwardly from throat 23. The entire inner surfaces of chamber 22, throat 23, overflow reservoir 24, and capillary channel 20 are coated with a suitable anticoagulant such as heparin to prevent the coagulation of blood 50 (FIG. 4). Blotter 26 is similarly treated for the same purpose.

A scale 30 is printed on the face of basal element 12 adjacent capillary channel 20 and provides an instant, visual indication of the hematocrit obtained through the use of blood sample apparatus 10 as will be discussed more fully hereinafter. Scale 30 is possible for the purpose of reading directly the resulting hematocrit only because overflow reservoir 24 is present to thereby provide an essentially fixed upper limit to the column of blood 50 (FIG. 4) in capillary channel 20.

The entire face of basal element 12 is covered with an adhesive coating 32. Adhesive coating 32 is designed to sealingly engage transparent cover 14 to basal element 12. Cover 14 encloses capillary channel 20 to create capillary tube 21 (FIG. 5) in basal element 12. An overlay 16 is releasably placed over the portion of adhesive coating 32 surrounding chamber 22 to prevent the corresponding portion of transparent cover 14 from being sealingly engaged to basal element 12 until the appropriate time. Overlay 16 also protects blotter 26 as well as chamber 22 and overflow reservoir 24 from contamination from dust, or the like.

Transparent cover 14 is configured to dimensionally correspond to basal element 12 and includes a bar code 34 and a writing surface 36. Bar code 34 is any suitable, machine readable indicia for enabling an operator (not shown) to keep track of blood sample apparatus 10. Writing surface 36 also enables the operator to suitably write on blood sample apparatus 10 thereby providing additional convenience in its use. Basal element 12 includes a hole 13 in the end thereof. Transparent cover 14 also includes a corresponding hole 15. Hole 15 is in alignment with hole 13 when transparent cover 14 is surmounted on basal element 12.

Figure 2:
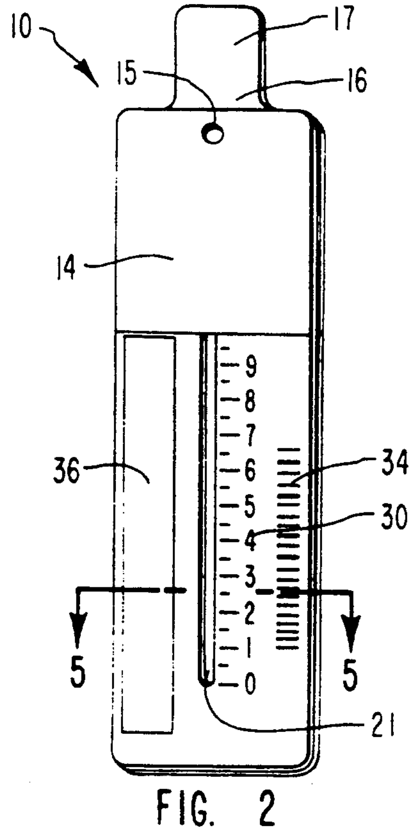
FIG. 2 is a plan view of the assembled hematocrit apparatus of FIG. 1.

Referring now to FIG. 2, the assembled configuration of blood sample apparatus 10 is shown having transparent cover 14 surmounted on basal element 12 with overlay 16 interposed across the upper end of basal element 12. Overlay 16 includes a tab 17 which extends beyond the external periphery of blood sample apparatus 10 and provides a convenient handle by which overlay 16 may be grasped in order to pull overlay 16 from adhesive layer 32 (FIGS. 1 and 3) where it has been releasably held prior to use of blood sample apparatus 10 as will be discussed more fully hereinafter.

For purposes of clarity in illustrating this invention, transparent cover 14 is shown without the customary shading to indicate transparency. Further, all of the underlying features of basal element 12 are shown as solid lines rather than being shown in lighter lines as seen through transparent cover 14 in order to avoid confusion. This is important since the clear visibility through transparent cover 14 is an important feature of this invention.

Figure 3:
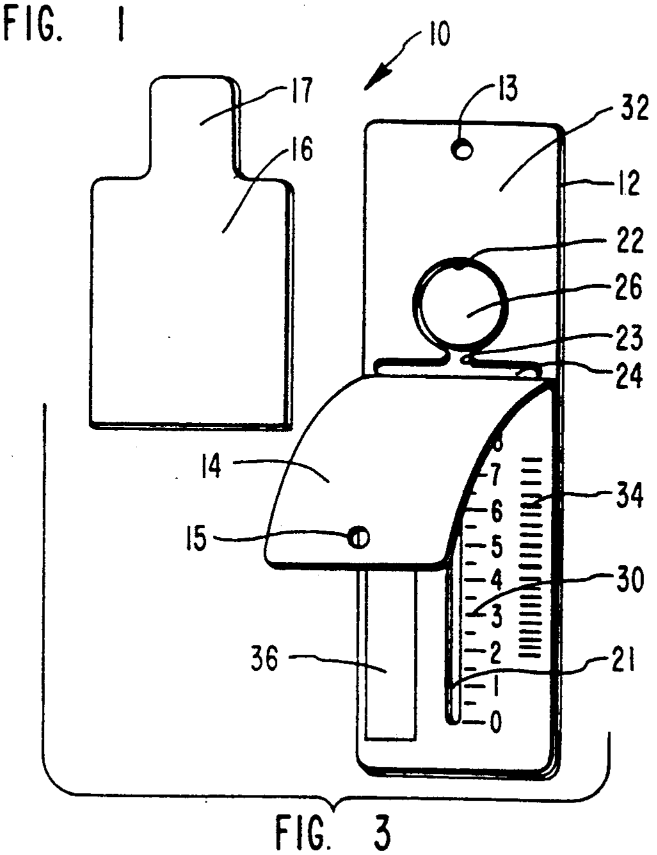
FIG. 3 is an exploded plan view of the hematocrit apparatus opened to receive a drop of blood.

With reference to FIG. 3, blood sample apparatus 10 is shown prepared for use in that overly 16 has been removed from adhesive layer 32 to expose blotter element 26. In this configuration with transparent cover 14 folded back as shown, the operator (not shown) is able to touch blotter element 26 against a drop of blood 50 (FIG. 4) causing the same to be drawn into blotter element 26 by the wick action therein. Thereafter, transparent cover 14 is closed across all of blotter element 26, chamber 26, and overflow reservoir 24. In this manner, blood 50 (FIG. 4) is entirely enclosed within blood sample apparatus 10.

Referring now to FIG. 4, the closed configuration of blood sample apparatus 10 is shown with transparent cover 14 superimposed on top of basal element 12 with hole 15 in alignment with hole 13. Hematocrit apparatus 10 is then placed in a centrifuge apparatus (not shown) and blood 50 is subjected to centrifugation. During the initial phase of centrifugation, blood 50 migrates under centrifugal force into capillary tube 21 until capillary tube 21 is filled after which blood 50 spreads out laterally into overflow reservoir 24 creating an extended upper surface 52. The dimensions of overflow reservoir 24 are such that the area of upper surface 52 is many times that of the cross sectional area of capillary tube 21. Accordingly, the surplus portion of blood 50, beyond that necessary to fill capillary tube 21, is spread across the adjacent surface of overflow reservoir 24. This means that if even a significant excess of blood 50 is present, the effective increase in the total length of the column of blood 50 in capillary tube 21 is minimal. Scale 30 is, therefore, readily usable to provide an accurate reading of the hematocrit of blood 50. After centrifugation of blood 50, the red blood cells 54 are packed into the lower portion of capillary tube 21 leaving a relatively clear supernatant fluid, plasma 56, at the upper end of capillary tube 21. An interface 55 between red blood cells 54 and plasma 56 serves as the cursor against which the hematocrit reading is obtained from scale 30. Interface 55 can also be subjected to further examination to ascertain the presence of malaria.

Blood sample apparatus 10 can then be discarded into a suitable infectious waste receptacle or even inserted into the individual patient's chart. This latter step is possible since blood 50 is safely sealed inside blood sample apparatus 10. Blood sample apparatus 10 is essentially unbreakable and the sealing relationship between transparent cover 14 and basal element 12 is permanent.

The Method

The operator (not shown) practices the method of this novel invention by obtaining blood sample apparatus 10 and noting on writing surface 36 the desired information such as the name of the patient, date, and time of collection of blood sample 50. Tab 17 is pulled to remove overlay 16 from adhesive layer 32 while at the same time pulling transparent cover 14 upwardly as shown in FIG. 3. Overlay 16 is then discarded and transparent cover 14 is folded downwardly to expose blotter element 26 to a drop of blood 50. Advantageously, the operator (not shown) is able to touch blotter element 26 to a drop of blood 50 without being unduly exposed to accidental contact with blood 50. After blood 50 has been drawn into blotter element 26, transparent cover 14 is extended across blotter element 26 and sealingly engaged to basal element 12 by adhesive layer 32.

Blood sample apparatus 10 now has blood 50 safely isolated inside its confines thereby effectively eliminating all danger of contact with blood 50. Accordingly, blood sample apparatus 10 can be safely and easily transported from place to place without undue risk of accidental contamination of the adjacent environment or personnel handling hematocrit apparatus 10.

Hole 13 in combination with hole 15 provides an anchor mechanism for releasably engaging blood sample apparatus 10 to a centrifuge apparatus (not shown). This feature is particularly important if basal element 12 is fabricated from a flexible plastic material and of lesser importance if basal element 12 is fabricated from a rigid plastic material. Holes 13 and 15 also adapt blood sample apparatus 10 to being tied by a lanyard (not shown) to a patient's chart, for example.

Centrifugation of blood sample apparatus 10 forces blood 50 out of blotter element 26 and into capillary tube 21 until capillary tube 21 becomes filled. Surplus blood 50 is then received into overflow reservoir 24 where it is spread out forming upper surface 52. Upper surface 52 closely approximates the upper end of capillary tube 21 thereby readily adapting blood sample apparatus 10 to include scale 30 as the nomogram for reading the resultant hematocrit.

Continued centrifugation of hematocrit apparatus 10 causes sedimentation of red blood cells 54 into the lower end of capillary tube 21 leaving plasma 56 at the upper end of capillary tube 21 with the upper end of red blood calls 54 forming a clearly defined interface 55. Interface 55 provides an easily observable cursor against which one is easily able to read the corresponding mark on scale 30 to thereby obtain directly a reading of the hematocrit of blood 50.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A capillary tube carrier apparatus for individually handling a sample of blood and determining the hematocrit of the sample of blood by centrifugation, said capillary tube carrier being transportable from place to place and comprising:

a basal element having an upper end and a lower end;

a capillary channel formed in said basal element between said upper end and said lower end, said capillary channel having an entrance adjacent said upper end;

an overflow reservoir adjacent said entrance to said capillary channel, said overflow reservoir being in fluid communication with said capillary channel at said entrance and extending transversely to said capillary channel to provide an increased surface area in comparison with the cross sectional area of said capillary channel;

a chamber formed adjacent said upper end for receiving a sample of blood, said chamber being in alignment with and in fluid communication with said capillary channel through said entrance;

blotter means in said chamber, said blotter means comprising an absorbent material for releasably receiving the sample of blood;

a transparent overlay for said basal element, said transparent overlay enclosing said capillary channel to form a capillary tube while selectively covering said chamber; and centrifugation means for forcing the sample of blood from said blotter means in said chamber through said entrance into said capillary tube and separating red blood cells from plasma in the sample of blood to provide a hematocrit of the sample of blood, said overflow reservoir receiving surplus blood from the sample of blood after said capillary tube has been filled.

2. The capillary tube carrier apparatus defined in claim 1 wherein said basal element includes a calibration indicia adjacent said capillary channel, said calibration indicia providing a direct reading of said hematocrit of said sample of blood in said capillary tube.

3. The capillary tube carrier apparatus defined in claim 1 wherein said transparent overlay includes a surface upon which an indicia can be applied.

4. The capillary tube carrier apparatus defined in claim 1 wherein said transparent overlay includes a machine-readable indicia.

5. The capillary tube carrier apparatus defined in claim 1 wherein said transparent overlay also selectively encloses said chamber to sealingly enclose said sample of blood in said improved blood sample apparatus after said sample of blood has been placed in said chamber.

6. A capillary tube carrier apparatus for obtaining the hematocrit of a sample of blood therein by centrifugation of said capillary tube carrier apparatus comprising:

said capillary tube carrier apparatus comprising:

a planar basal element having an upper end and a lower end, said lower end being defined as the direction of the centrifugal forces imposed on said capillary tube carrier during centrifugation;

a chamber for receiving the sample of blood, said chamber being formed in said basal element;

a blood-receiving blotter means comprising an absorbent material in said chamber for releasably receiving the sample of blood;

a capillary channel formed in said basal element in fluid communication with said chamber and extending from said upper end to said lower end;

an overflow reservoir in fluid communication with said capillary channel between said chamber and said capillary channel; and a transparent overlay for said basal element, said transparent overlay forming a capillary tube by enclosing said capillary channel, said transparent overlay covering said overflow reservoir and selectively enclosing said chamber after the sample of blood has been received in said blood-receiving blotter means;

centrifugation means for forcing said sample of blood from said chamber into said capillary tube where the centrifugal forces of said centrifugation means separates red blood cells from plasma in the sample of blood to provide a reading of said the hematocrit of the sample of blood, said overflow reservoir receiving surplus blood in excess of blood required to fill said capillary tube from the sample of blood; and handling means for transporting said capillary tube carrier apparatus from place to place and for storing said sample of blood at a location remote from said centrifugation means.

7. The capillary tube carrier apparatus defined in claim 6 wherein said basal element includes a calibration indicia adjacent said capillary channel, said calibration indicia being visually readable to indicate said hematocrit of said sample of blood in said capillary tube.

8. The capillary tube carrier apparatus defined in claim 6 wherein said transparent overlay includes a surface upon which an indicia can be applied.

9. The capillary tube carrier apparatus defined in claim 6 wherein said transparent overlay includes a machine-readable indicia.

10. The capillary tube carrier apparatus defined in claim 6 wherein said transparent overlay also selectively encloses said chamber to sealingly enclose said sample of blood in said improved blood sample apparatus after said sample of blood has been deposited in said chamber.

11. A method for enclosing a sample of blood in a capillary tube carrier while obtaining the hematocrit reading thereof by centrifugation comprising:

constructing said capillary tube carrier comprising the steps of:

obtaining a basal element configured to be subjected to centrifugation, said basal element having an axis corresponding to the centrifugal forces imposed on said basal element during said centrifugation, said axis having an upper end and a lower end, said centrifugation providing said centrifugal forces toward said lower end;

forming a capillary channel in said basal element with an entrance at said upper end;

preparing a chamber in said basal element above said entrance at said upper end, said chamber being configured to receive the sample of blood and containing an absorbent material for releasably receiving the sample, said chamber being in fluid communication with said capillary channel through said entrance;

producing an overflow reservoir adjacent said entrance of said capillary channel and in fluid communication with said capillary channel; and creating a capillary tube out of said capillary channel by enclosing said capillary channel with a transparent overlay;

obtaining the hematocrit reading of said sample of blood comprising the steps of:

placing the sample of blood in said chamber;

subjecting the sample of blood to said centrifugation, said centrifugation forcing the sample of blood from said chamber into said capillary tube and separating the sample of blood into red blood cells and plasma thereby providing said hematocrit reading; and receiving excess blood in said overflow reservoir from the sample of blood after said capillary tube has been filled during said centrifugation; and transporting the sample of blood from place to place, the sample of blood being enclosed in said capillary tube carrier.

12. The method defined in claim 11 wherein said producing step includes placing a calibration indicia on said basal element adjacent said capillary channel said calibration indicia providing an indication of said hematocrit reading of said sample of blood.

13. The method defined in claim 11 wherein said placing step includes sealing the sample of blood in said chamber and said capillary tube with said transparent overlay.

14. The method defined in claim 11 wherein said creating step includes placing a surface upon which an indicia can be applied on said transparent overlay.

* * * * *